(12) United States Patent
Sutterlin, III et al.

(10) Patent No.: US 9,707,096 B2
(45) Date of Patent: Jul. 18, 2017

(54) SPINAL FIXATION DEVICE

(71) Applicant: K2M, Inc., Leesburg, VA (US)

(72) Inventors: Chester Evan Sutterlin, III, Longboat Key, FL (US); Ehud Mendel, Columbus, OH (US); Clint Boyd, Winchester, VA (US); Brandon Moore, Summit Point, WV (US); Scott Jones, McMurray, PA (US)

(73) Assignee: K2M, Inc., Leesburg, VA (US)

( * ) Notice: Subject to any disclaimer, the term of this patent is extended or adjusted under 35 U.S.C. 154(b) by 554 days.

(21) Appl. No.: 14/212,236

(22) Filed: Mar. 14, 2014

(65) Prior Publication Data

US 2014/0277503 A1 Sep. 18, 2014

Related U.S. Application Data

(60) Provisional application No. 61/781,837, filed on Mar. 14, 2013.

(51) Int. Cl.
*A61F 2/44* (2006.01)
*A61F 2/46* (2006.01)
*A61F 2/30* (2006.01)

(52) U.S. Cl.
CPC .......... *A61F 2/4465* (2013.01); *A61F 2/4611* (2013.01); *A61F 2002/3093* (2013.01); *A61F 2002/30373* (2013.01); *A61F 2002/30392* (2013.01); *A61F 2002/30405* (2013.01); *A61F 2002/30497* (2013.01); *A61F 2002/30523* (2013.01); *A61F 2002/30538* (2013.01); *A61F 2002/30556* (2013.01); *A61F 2002/30579* (2013.01); *A61F 2002/30601* (2013.01); *A61F 2002/30904* (2013.01); *A61F 2002/4623* (2013.01); *A61F 2002/4627* (2013.01); *A61F 2002/4638* (2013.01);

(Continued)

(58) Field of Classification Search
CPC ........ A61F 2/4455; A61F 2/446; A61F 2/447; A61F 2/4611; A61F 2/4465; A61F 2/44
USPC ............... 623/17.16, 17.11, 17.15; 606/86 A
See application file for complete search history.

(56) References Cited

U.S. PATENT DOCUMENTS

| 3,374,011 A | 3/1968 | Schipper |
| 3,402,947 A | 9/1968 | Lewis |

(Continued)

FOREIGN PATENT DOCUMENTS

| DE | 19804765 A1 | 8/1999 |
| EP | 1878408 A1 | 1/2008 |

(Continued)

OTHER PUBLICATIONS

European Search Report dated May 28, 2009 from corresponding EP Appln. No. EP09152270.6 filed Feb. 6, 2009.

(Continued)

*Primary Examiner* — Si Ming Ku
(74) *Attorney, Agent, or Firm* — Carter, DeLuca, Farrell & Schmidt, LLP (57) ABSTRACT

A spinal fixation device includes a body having a first end defining an aperture, an engaging portion configured to engage a vertebral body, and an adjustment member configured to be received in the body through the aperture. The adjustment member is operatively coupled with the engaging portion to selectively position the engaging portion at one of a plurality of orientations relative to the body.

24 Claims, 6 Drawing Sheets

(52) U.S. Cl.
CPC ............... *A61F 2310/00017* (2013.01); *A61F 2310/00023* (2013.01); *A61F 2310/00029* (2013.01); *A61F 2310/00179* (2013.01)

(56) References Cited

U.S. PATENT DOCUMENTS

| | | | |
|---|---|---|---|
| 3,588,023 A | 6/1971 | Cohen | |
| 3,893,730 A | 7/1975 | Homier et al. | |
| 4,387,926 A | 6/1983 | Van Eerden et al. | |
| 4,554,914 A | 11/1985 | Kapp et al. | |
| 4,938,319 A | 7/1990 | Ernst | |
| 5,053,036 A | 10/1991 | Perren et al. | |
| 5,108,066 A | 4/1992 | Lundstrom | |
| 5,236,460 A | 8/1993 | Barber | |
| 5,290,312 A | 3/1994 | Kojimoto et al. | |
| 5,336,223 A | 8/1994 | Rogers | |
| 5,360,430 A | 11/1994 | Lin | |
| 5,458,641 A | 10/1995 | Ramirez Jimenez | |
| 5,520,690 A | 5/1996 | Errico et al. | |
| 5,547,308 A | 8/1996 | Wright | |
| 5,571,190 A | 11/1996 | Ulrich et al. | |
| 5,571,192 A | 11/1996 | Schonhoffer | |
| 5,702,455 A | 12/1997 | Saggar | |
| 5,723,013 A | 3/1998 | Jeanson et al. | |
| 5,738,685 A | 4/1998 | Halm et al. | |
| 5,776,198 A | 7/1998 | Rabbe et al. | |
| 5,885,286 A | 3/1999 | Sherman et al. | |
| 5,888,014 A | 3/1999 | Lung et al. | |
| 5,901,798 A | 5/1999 | Herrera et al. | |
| 5,904,683 A | 5/1999 | Pohndorf et al. | |
| 5,980,522 A | 11/1999 | Koros et al. | |
| 5,989,290 A | 11/1999 | Biedermann et al. | |
| 6,074,391 A | 6/2000 | Metz-Stavenhagen et al. | |
| 6,099,531 A | 8/2000 | Bonutti | |
| 6,110,172 A | 8/2000 | Jackson | |
| 6,132,434 A | 10/2000 | Sherman et al. | |
| 6,176,881 B1 | 1/2001 | Schar et al. | |
| 6,179,514 B1 | 1/2001 | Cheng | |
| 6,183,517 B1 | 2/2001 | Suddaby | |
| 6,193,755 B1 | 2/2001 | Metz-Stavenhagen et al. | |
| 6,193,756 B1 | 2/2001 | Studer et al. | |
| 6,200,348 B1 | 3/2001 | Biedermann et al. | |
| 6,235,062 B1 | 5/2001 | Gramnas | |
| 6,241,769 B1 | 6/2001 | Nicholson et al. | |
| 6,254,602 B1 | 7/2001 | Justis | |
| 6,273,888 B1 | 8/2001 | Justis | |
| 6,296,642 B1 | 10/2001 | Morrison et al. | |
| 6,296,665 B1 | 10/2001 | Strnad et al. | |
| 6,302,888 B1 | 10/2001 | Mellinger et al. | |
| 6,332,895 B1 | 12/2001 | Suddaby | |
| 6,342,074 B1 | 1/2002 | Simpson | |
| 6,364,880 B1 | 4/2002 | Michelson | |
| 6,375,683 B1 | 4/2002 | Crozet et al. | |
| 6,395,034 B1 | 5/2002 | Suddaby | |
| 6,419,705 B1 | 7/2002 | Erickson | |
| 6,423,063 B1 | 7/2002 | Bonutti | |
| 6,440,170 B1 | 8/2002 | Jackson | |
| 6,500,178 B2 | 12/2002 | Zucherman et al. | |
| 6,524,341 B2 | 2/2003 | Lang et al. | |
| 6,558,423 B1 | 5/2003 | Michelson | |
| 6,562,074 B2 | 5/2003 | Gerbec et al. | |
| 6,610,090 B1 | 8/2003 | Bohm et al. | |
| 6,616,695 B1 | 9/2003 | Crozet et al. | |
| 6,629,998 B1 | 10/2003 | Lin | |
| 6,648,917 B2 | 11/2003 | Gerbec et al. | |
| 6,660,038 B2 | 12/2003 | Boyer, II et al. | |
| 6,663,060 B1 | 12/2003 | Gifford, Sr. | |
| 6,716,214 B1 | 4/2004 | Jackson | |
| 6,730,088 B2 | 5/2004 | Yeh | |
| 6,752,832 B2 | 6/2004 | Neumann | |
| 6,770,096 B2 | 8/2004 | Bolger et al. | |
| 6,827,719 B2 | 12/2004 | Ralph et al. | |
| 6,830,589 B2 | 12/2004 | Erickson | |
| 6,834,840 B1 | 12/2004 | Metz et al. | |
| 6,835,196 B2 | 12/2004 | Biedermann et al. | |
| 6,837,889 B2 | 1/2005 | Shluzas | |
| 6,843,791 B2 | 1/2005 | Serhan | |
| 6,852,129 B2 | 2/2005 | Gerbec et al. | |
| 6,863,673 B2 | 3/2005 | Gerbec et al. | |
| 6,866,682 B1 | 3/2005 | An et al. | |
| 6,869,112 B2 | 3/2005 | Guidetti | |
| 6,869,433 B2 | 3/2005 | Glascott | |
| 6,884,244 B1 | 4/2005 | Jackson | |
| 6,893,443 B2 | 5/2005 | Frigg et al. | |
| 6,896,677 B1 | 5/2005 | Lin | |
| 6,908,485 B2 | 6/2005 | Crozet et al. | |
| 6,918,911 B2 | 7/2005 | Biedermann et al. | |
| 6,945,975 B2 | 9/2005 | Dalton | |
| 6,972,019 B2 | 12/2005 | Michelson | |
| 6,984,234 B2 | 1/2006 | Bray | |
| 7,001,385 B2 | 2/2006 | Bonutti | |
| 7,025,787 B2 | 4/2006 | Bryan et al. | |
| 7,033,394 B2 | 4/2006 | Michelson | |
| 7,041,135 B2 | 5/2006 | Michelson | |
| 7,052,499 B2 | 5/2006 | Steger et al. | |
| 7,056,343 B2 | 6/2006 | Schafer et al. | |
| 7,077,864 B2 | 7/2006 | Byrd, III et al. | |
| 7,086,631 B2 | 8/2006 | Lee et al. | |
| 7,087,057 B2 | 8/2006 | Konieczynski et al. | |
| 7,094,257 B2 | 8/2006 | Mujwid et al. | |
| 7,156,874 B2 | 1/2007 | Paponneau et al. | |
| 7,175,624 B2 | 2/2007 | Konieczynski et al. | |
| 7,229,443 B2 | 6/2007 | Eberlein et al. | |
| 7,285,134 B2 | 10/2007 | Berry et al. | |
| 7,318,825 B2 | 1/2008 | Butler et al. | |
| 7,445,627 B2 | 11/2008 | Hawkes et al. | |
| 7,527,640 B2 | 5/2009 | Ziolo et al. | |
| 7,531,002 B2 | 5/2009 | Sutton et al. | |
| 7,544,208 B1 | 6/2009 | Mueller et al. | |
| 7,611,104 B1 | 11/2009 | Gifford, Sr. | |
| 7,618,456 B2 | 11/2009 | Mathieu et al. | |
| 7,651,517 B2 | 1/2010 | Konieczynski et al. | |
| 7,691,147 B2 | 4/2010 | Gutlin et al. | |
| 7,862,616 B2 | 1/2011 | Lechmann et al. | |
| 8,137,405 B2 | 3/2012 | Kostuik et al. | |
| 8,353,961 B2 | 1/2013 | McClintock et al. | |
| 8,377,101 B2 | 2/2013 | Barrus et al. | |
| 8,439,977 B2 | 5/2013 | Kostuik et al. | |
| 8,585,761 B2 | 11/2013 | Theofilos | |
| 8,663,330 B2 | 3/2014 | McClintock et al. | |
| 8,673,011 B2 | 3/2014 | Theofilos et al. | |
| 8,801,791 B2 | 8/2014 | Soo et al. | |
| 2001/0021851 A1 | 9/2001 | Eberlein et al. | |
| 2002/0032443 A1 | 3/2002 | Sherman et al. | |
| 2002/0128654 A1 | 9/2002 | Steger et al. | |
| 2002/0161441 A1 | 10/2002 | Lang et al. | |
| 2003/0130737 A1 | 7/2003 | McGahan et al. | |
| 2003/0130739 A1 | 7/2003 | Gerbec et al. | |
| 2003/0181980 A1 | 9/2003 | Berry et al. | |
| 2004/0186569 A1* | 9/2004 | Berry .................. A61F 2/44 623/17.11 |
| 2004/0247379 A1 | 12/2004 | Guidetti | |
| 2005/0060034 A1 | 3/2005 | Berry et al. | |
| 2005/0085910 A1 | 4/2005 | Sweeney | |
| 2005/0209697 A1 | 9/2005 | Paponneau et al. | |
| 2005/0218275 A1 | 10/2005 | Keating | |
| 2005/0273173 A1 | 12/2005 | Gordon et al. | |
| 2006/0041260 A1 | 2/2006 | Orbay | |
| 2006/0074490 A1 | 4/2006 | Sweeney | |
| 2006/0100710 A1 | 5/2006 | Gutlin et al. | |
| 2006/0122701 A1 | 6/2006 | Kiester | |
| 2006/0129244 A1 | 6/2006 | Ensign | |
| 2006/0149251 A1 | 7/2006 | Ziolo et al. | |
| 2006/0149385 A1 | 7/2006 | McKay | |
| 2006/0173456 A1 | 8/2006 | Hawkes et al. | |
| 2006/0200244 A1 | 9/2006 | Assaker | |
| 2006/0212118 A1 | 9/2006 | Abernathie | |
| 2006/0217715 A1 | 9/2006 | Serhan et al. | |
| 2006/0241762 A1* | 10/2006 | Kraus ................. A61F 2/4611 623/17.11 |
| 2006/0241770 A1 | 10/2006 | Rhoda et al. | |
| 2006/0271047 A1 | 11/2006 | Jackson | |
| 2006/0276792 A1 | 12/2006 | Ensign et al. | |
| 2007/0010887 A1 | 1/2007 | Williams et al. | |

(56) References Cited

U.S. PATENT DOCUMENTS

| | | |
|---|---|---|
| 2007/0032871 A1 | 2/2007 | Michelson |
| 2007/0073298 A1 | 3/2007 | Beutter et al. |
| 2007/0093817 A1 | 4/2007 | Barrus et al. |
| 2007/0100340 A1 | 5/2007 | Lange et al. |
| 2007/0106231 A1 | 5/2007 | Snow et al. |
| 2007/0162126 A1 | 7/2007 | Karahalios et al. |
| 2007/0191954 A1 | 8/2007 | Hansell et al. |
| 2007/0219635 A1 | 9/2007 | Mathieu et al. |
| 2007/0250171 A1 | 10/2007 | Bonin |
| 2007/0255408 A1 | 11/2007 | Castleman et al. |
| 2007/0270964 A1 | 11/2007 | Strohkirch et al. |
| 2007/0270968 A1 | 11/2007 | Baynham et al. |
| 2007/0282441 A1 | 12/2007 | Stream et al. |
| 2008/0009946 A1 | 1/2008 | Douget et al. |
| 2008/0021555 A1 | 1/2008 | White et al. |
| 2008/0114467 A1 | 5/2008 | Capote et al. |
| 2008/0125864 A1 | 5/2008 | de Villiers et al. |
| 2008/0147193 A1* | 6/2008 | Matthis ................ A61F 2/4425 623/17.16 |
| 2008/0167720 A1 | 7/2008 | Melkent |
| 2008/0249624 A1 | 10/2008 | Josimovic-Alasevic et al. |
| 2008/0249625 A1 | 10/2008 | Waugh et al. |
| 2008/0288071 A1 | 11/2008 | Biyani et al. |
| 2010/0005715 A1 | 1/2010 | Allsop et al. |
| 2010/0137919 A1 | 6/2010 | Wolter |
| 2011/0160861 A1* | 6/2011 | Jimenez ................ A61F 2/4465 623/17.16 |

FOREIGN PATENT DOCUMENTS

| | | |
|---|---|---|
| FR | 2902315 A1 | 12/2007 |
| SU | 1560184 A1 | 4/1990 |
| WO | 98/46173 A1 | 10/1998 |
| WO | 03/032812 A2 | 4/2003 |
| WO | 2008005627 A2 | 1/2008 |
| WO | 2009023016 A1 | 2/2009 |

OTHER PUBLICATIONS

ISR from Int'l Application No. PCT/US2009/038787 dated May 27, 2009.
ISR from Int'l Application No. PCT/US2009/038780 dated Nov. 13, 2009.
European Search Report for EP 09 72 4564 dated Dec. 7, 2012.
European Search Report EP15194277 dated Mar. 3, 2016.
European Communication issued in corresponding European Appln. No. 15194277.8 dated Feb. 23, 2017.

* cited by examiner

SPINAL FIXATION DEVICE

CROSS-REFERENCE TO RELATED APPLICATION

This application claims priority to, and the benefit of, U.S. Provisional Patent Application Ser. No. 61/781,837, filed on Mar. 14, 2013, the entire contents of which are incorporated by reference herein.

BACKGROUND

Technical Field

The present disclosure relates to an apparatus for treating spinal conditions, and more particularly, to an intervertebral implant.

Background of Related Art

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two winglike projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as inter-vertebral discs. Inter-vertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

Disorders of the spine that may cause misalignment of the vertebrae or constriction of the spinal canal include spinal injuries, infections, tumor formation, herniation of the inter-vertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina, i.e., the bony roof of the spinal canal. Discectomy involves removal of the inter-vertebral discs. Corpectomy involves removal of the vertebral body as well as the adjacent inter-vertebral discs.

A number of spinal surgical devices may be used to promote bony fusion after decompressing the spinal nerves. For instance, surgeons often replace the diseased vertebral tissue with one or more spinal cages and bone support matrix. Spinal cages support adjacent vertebral segments, while furthering spinal fusion of adjacent vertebral bodies. Scientists and clinicians have developed a number of devices and methods for decompressing spinal nerves. Improvements to these methods and devices are nevertheless still possible.

Furthermore, intervertebral spacer implants used as a stand-alone device or provided in an assembly including a retention mechanism to help alleviate expulsion and movement of the implant when placed in the spine, are well known. Such implant assemblies are advantageous in providing an implant that is easier to insert in the spine. Intervertebral spacer implant assemblies which include a spacer and a plate, where the plate comprises a supplemental or alternative retention mechanism having one or more holes in the anterior end of the plate that are directed toward the superior, inferior or both end plates of adjacent vertebrae are also known in the art. Such implants are used to stabilize and immobilize the spinal segments in the treatment of single or multi-level degenerative disc disease, spinal stenosis, and failed previous fusions, as well as other spine conditions.

To meet the problem of preventing expulsion of the interbody device and for providing stability to the anatomy, a need exists for an spinal fixation device that can be secured to the spine and provide anterior column support and stabilization, while providing a maximum fusion area.

SUMMARY

In accordance with an embodiment of the present disclosure, there is provided a spinal fixation device including a body, an engaging portion configured to engage a vertebral body, and an adjustment member. The body has a first end defining an aperture. The adjustment member is slidably received in the body through the aperture. The adjustment member is operatively coupled with the engaging portion to selectively position the engaging portion at one of a plurality of orientations relative to the body.

In an embodiment, the adjustment member may include first and second supporting members operatively coupled with the engaging portion. In particular, the first and second supporting members may be movable relative to each other. The first supporting member may have a camming rod slidably engaging a camming slot defined in the engaging portion. The second supporting member may include a rod. The engaging portion may be coupled rotatably with the rod. The first supporting member of the adjustment member may include threads disposed along a length of the first supporting member. The threads may be configured to selectively position the first supporting member at one of a plurality of positions along a longitudinal axis defined by the body. The second supporting adjustment member may include threads disposed along a length of the second supporting member. The threads may be configured to selectively position the second supporting member at one of a plurality of positions along the longitudinal axis.

The body may include a first retaining member rotatably supported in the body. The first retaining member may include internal threads configured to engage the threads on the first and second supporting members. The first retaining member may include a circumferential groove and a radially expandable retaining ring. The retaining ring may be positioned in the circumferential groove.

In another embodiment, the body may include an annular groove configured to receive at least a portion of the retaining ring. The body may include a plurality of bores configured to receive a screw. The plurality of bores may be arranged circumferentially on side walls of the body. The first supporting member may include a plurality of bores defined along a length thereof. The second supporting member may include a plurality of bores defined along a length thereof. At least one of the plurality of bores defined in the body may be aligned with at least one of the bores defined in the first and second supporting members. In addition, the engaging portion may include a plurality of protrusions configured to grip the vertebral body. The second end of the body may be configured to engage the vertebral body.

In yet another embodiment, the body may further include a second retaining member rotatably supported in the body. The second retaining member may include internal threads configured to engage the threads on the first and second supporting members. In addition, the first and second retaining members may each include a plurality of teeth opposing each other.

In accordance with another embodiment of the present disclosure, there is provided a spinal fixation system including a spinal fixation device and an insertion instrument. The spinal fixation device includes a body having a first end defining an aperture, a first engaging portion configured to engage a vertebral body, and an adjustment member configured to be received in the body through the aperture. The first engaging portion is rotatably coupled with the adjustment member to be selectively positioned at one of a plurality of orientations relative to the body. The insertion instrument has an elongate member including first and second rods configured to releasably engage the body.

In an embodiment, the body may include a pair of bores configured to receive a screw. The first and second rods may be configured to engage the pair of bores. The second rod may threadably engage one of the pair of bores. The adjustment member may include first and second supporting members operatively coupled with the first engaging portion. The first and second supporting members may be movable relative to each other.

In another embodiment, the spinal fixation device may further include a first retaining member rotatably supported in the body. The first retaining member may include internal threads configured to engage threads on the adjustment member. The first retaining member may include a plurality of teeth extending along a longitudinal axis defined by the body. The plurality of teeth may be operatively coupled with the first rod of the insertion instrument such that rotation of the first rod causes rotation of the first retaining member about the longitudinal axis, which, in turn, may cause an axial movement of the adjustment member.

BRIEF DESCRIPTION OF THE DRAWINGS

The above and other aspects and features of the present disclosure will become more apparent in light of the following detailed description when taken in conjunction with the accompanying drawings in which.

DETAILED DESCRIPTION OF THE EMBODIMENTS

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" is used in this application to indicate a direction toward a patient's head, whereas the term "caudad" indicates a direction toward the patient's feet. Moreover, the term "medial" indicates a direction toward the middle of the body of the patient, while the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

With reference to FIGS. 1-4, an embodiment of the present disclosure is shown generally as a spinal fixation device 100 configured and adapted to be positionable between vertebral bodies to support vertebral bodies and to promote spinal fusion. Spinal fixation device 100 includes a generally elongate body 110, first and second engaging portions 140, 150 configured to engage end plates of adjacent vertebral bodies, and an elongate adjustment arm 160 (FIG. 6) operatively coupled with first engaging portion 140. First and second engaging portions 140, 150 are configured to engage, e.g., endplates of superior and inferior vertebral bodies, respectively. Each of first and second engaging portions 140, 150 defines ridges 133a, 133b (FIGS. 5a and 5b) or similar projections to aid in securing spinal fixation device 100 to the vertebral bodies for enhanced gripping of the vertebral bodies and minimizing movement of spinal fixation device 100 relative to the vertebral bodies. Elongate adjustment arm 160 may be selectively positioned relative to body 110 to achieve a desired lordosis of first engaging portion 140 and a desired distance between body 110 and first engaging portion 140, as will be discussed hereinbelow.

Spinal fixation device 100 may be made of titanium, titanium alloy, stainless steel, allograft bone, autologous bone graft, polyetheretherketone (PEEK), cobalt chrome, polymeric materials, a combination thereof, or any other suitable biocompatible material. In particular, spinal fixation device 100 may be formed of bone, or an artificial material other than bone which may be harder or stronger than bone, such as, e.g., ceramic materials. Body 110 may include a bone growth promoting material such as, e.g., bone morphogenic protein and hydroxyapatite. Body 110 may define a cavity 151 to accommodate bone graft material therein.

Figures 1, 2:
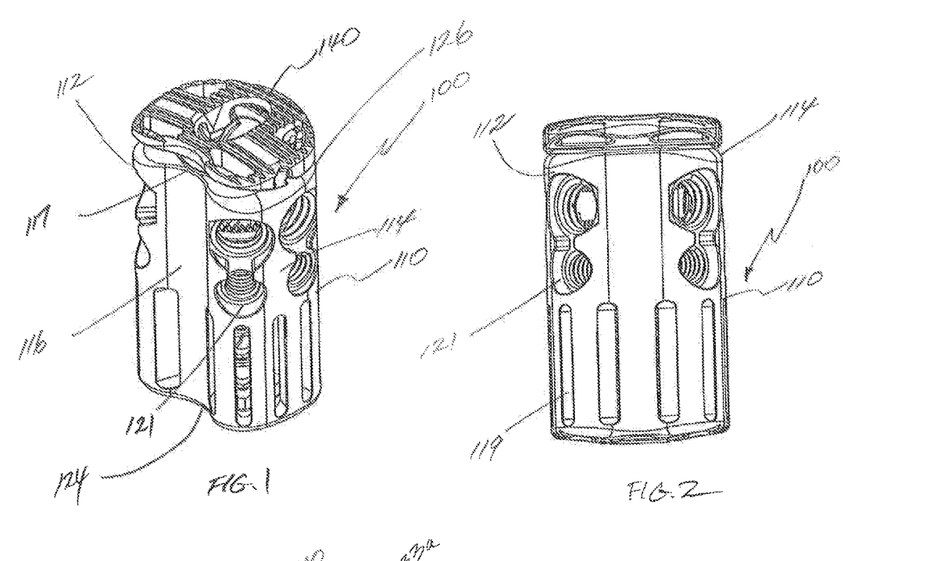
FIG. 1 is a perspective view of a spinal fixation device in accordance with an embodiment of the present disclosure.
FIG. 2 is a front view of the spinal fixation device of FIG. 1.
Figures 3, 4:
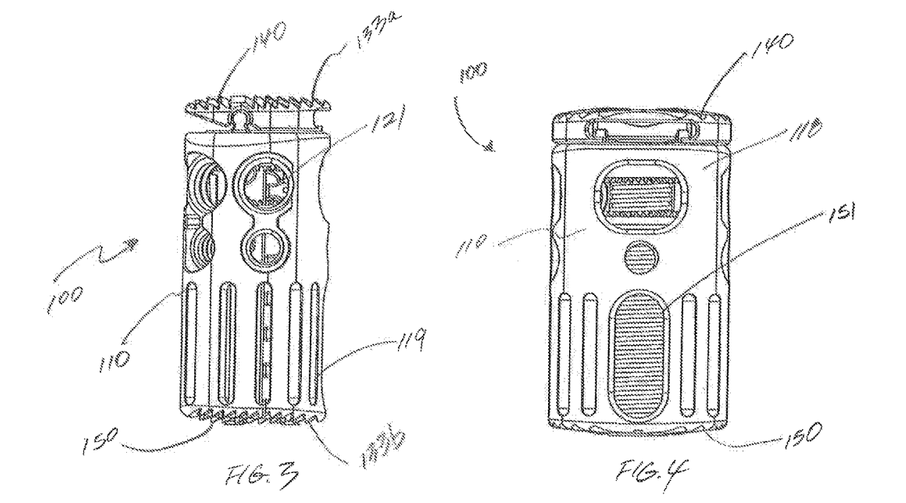
FIG. 3 is a side view of the spinal fixation device of FIG. 1.
FIG. 4 is a rear view of the spinal fixation device of FIG. 1.
Figure 5A:
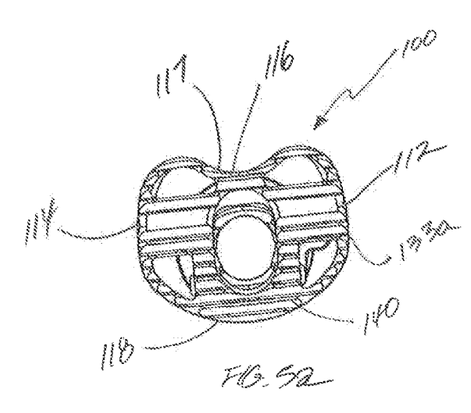
FIG. 5a is a top view of the spinal fixation device of FIG. 1.
Figure 5B:
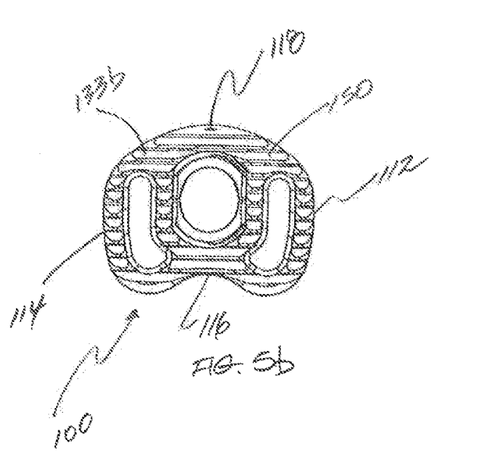
FIG. 5b is a bottom view of the spinal fixation device of FIG. 1.
Figures 6, 7:
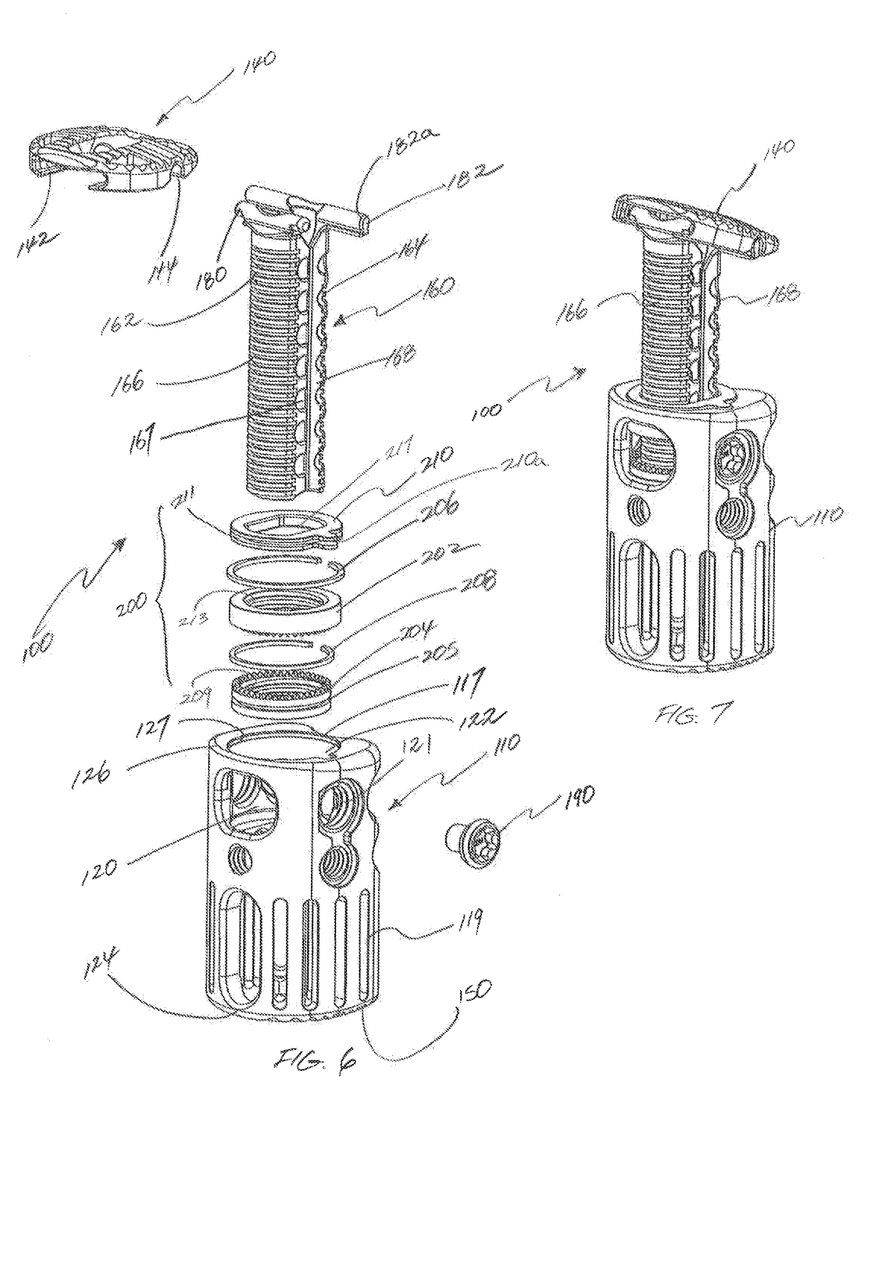
FIG. 6 is a exploded, perspective view of the spinal fixation device of FIG. 1 with parts separated.
FIG. 7 is a perspective view of the spinal fixation device of FIG. 1 with a first engaging portion spaced apart from a body of the spinal fixation device.

With reference to FIGS. 5a, 5b, and 6, body 110 includes first and second ends 124, 126 and first, second, third, and fourth walls 112, 114, 116, 118 extending between first and second ends 124, 126. Walls 112, 114, 116, 118 collectively define chamber 120. First and second walls 112, 114 have generally rounded outer surfaces and are symmetrically arranged. First and second walls 112, 113 include a plurality of bores 121 configured to receive a screw 190 and a surgical instrument 1000 (FIG. 10), as will be discussed hereinbelow. Bores 121 are circumferentially arranged to facilitate insertion of screw 190 and engagement with insertion instrument 1000 at different orientations. In an embodiment, a pair of bores 121 is longitudinally aligned to selectively secure elongate adjustment arm 160, as will be described hereinbelow. In an embodiment, bore 121 and screw 190 may be threadably engaged. Third and fourth walls 116, 118 oppose each other and interconnect first and second walls 112, 114. Third wall 116 includes a cutout portion 117, and fourth wall 118 includes a rounded outer surface. In addition, body 110 defines a plurality of slots 119 extending along a portion of a length of body 110.

Figure 9:
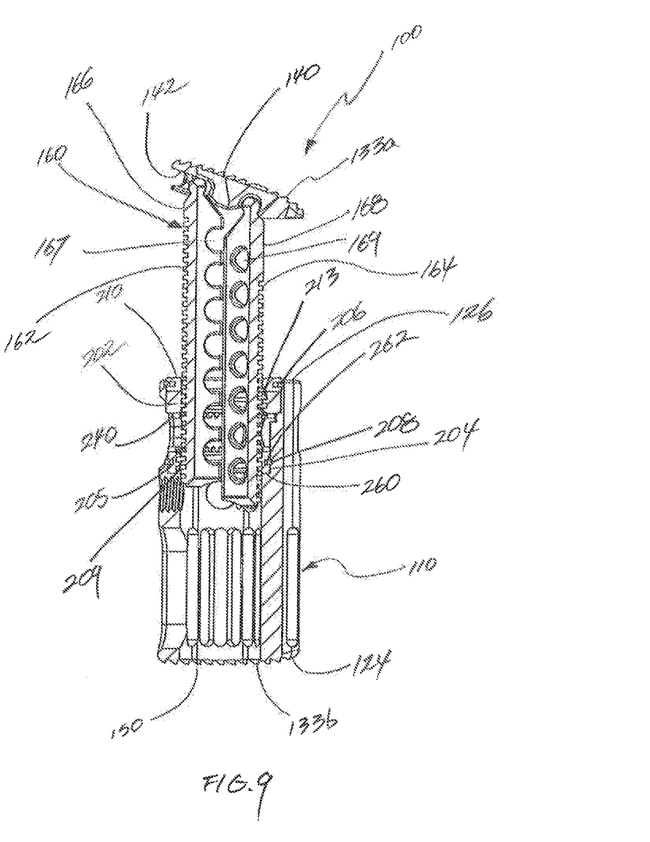
FIG. 9 is a cross-sectional view of the spinal fixation device of FIG. 8 cut along a section line "9-9" in FIG. 8.

With particular reference to FIGS. 6 and 9, first end 124 of body 110 has second engaging portion 150 attached thereto, and second end 126 defines an aperture 122. Chamber 120 is configured to receive at least a portion of elongate adjustment arm 160 through aperture 122. Elongate adjustment arm 160 is selectively positionable within chamber 120. Elongate adjustment arm 160 is mounted in chamber 120 by mounting assembly 200. Mounting assembly 200 includes first and second retaining portions 202, 204, first and second retaining ring 206, 208, and a cover 210.

With reference to FIGS. 6 and 9, an inner surface of body 110 includes a first shoulder portion 240 configured to rotatably support first retaining portion 202 thereon. Cover 210 defines a non-circular aperture 217 substantially complementary to a transverse cross-section of elongate adjustment arm 160 to inhibit rotation of elongate adjustment arm 160 in aperture 217. In addition, cover 210 includes a finger 210a to inhibit rotation of cover 210 with respect to body 110. First retaining portion 202 is rotatably interposed between cover 210 and first shoulder portion 240. In particular, cover 210 includes a circumferential groove 211 (FIG. 6) configured to retain at least a portion of first retaining ring 206. A portion of first retaining ring 206 extends radially outward from circumferential groove 211 and is received within an annular groove 127 (FIG. 6) defined adjacent second end 126 of body 110. First retaining ring 206 is radially movable. Under such a configuration, cover 210 is releasably attached to second end 126. The inner surface of body 110 further includes a second shoulder portion 260 configured to support second retaining portion 204 thereon. Second retaining portion 204 defines a circumferential groove 205 configured to receive at least a portion of second retaining ring 208. Second retaining ring 208 is disposed within circumferential groove 205 and extends radially outward therefrom. A portion of second retaining ring 208 is received within an annular groove 262 defined in the inner surface of body 110. Similar to first retaining ring 206, second retaining ring 208 is configured to deflect radially. Under such a configuration, second retaining portion 204 is rotatably mounted in body 110.

First and second retaining portions 202, 204 are rotatably supported in body 110. First shoulder portion 240 and cover 210 inhibit axial movement of first retaining portion 202. Second retaining ring 208 and circumferential groove 205, as well as second shoulder 260, inhibit axial movement of second retaining portion 204. First and second retaining portions 202, 204 include internal threads 213, 209 (FIG. 6), respectively. In particular, internal threads 209, 213 are in opposite directions, such that when first and second retaining portions 202, 204 rotate in opposite directions, the directions of internal threads 209, 213 are the same. In particular, internal threads 209, 213 are configured to threadably engage outer threads 162, 164 of first and second portions 166, 168 of elongate adjustment arm 160, respectively. Under such a configuration, rotation of first and second retaining portions 202, 204 in opposite directions causes axial movement of elongate adjustment arm 160 along longitudinal axis "A-A", as will be described hereinbelow. In addition, first and second retaining portions 202, 204 include opposing teeth 268, 266 (FIG. 8), respectively. Teeth 266, 268 are configured to engage an engaging portion 1032 of a surgical instrument 1000 (FIG. 10), as will be discussed hereinbelow. Under such a configuration, rotation of engaging portion 1032 operatively coupled with teeth 266, 268 causes rotation of first and second retaining portions 202, 204, which, in turn, causes axial movement of elongate adjustment arm 160.

Figure 8:
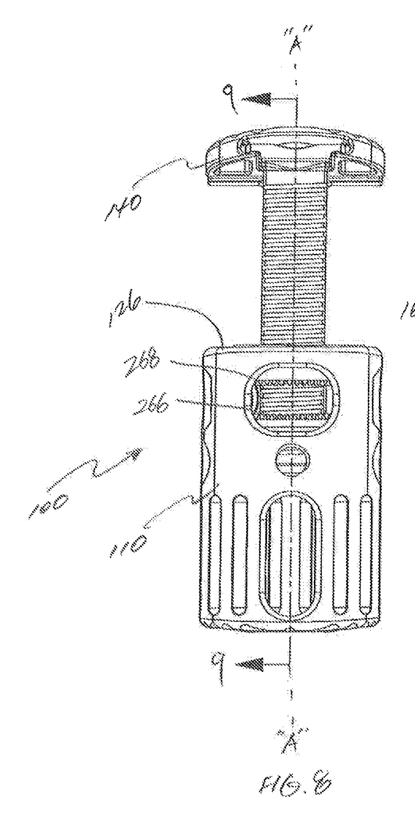
FIG. 8 is a rear view of the spinal fixation device of FIG. 7.

With continuing reference to FIG. 6, elongate adjustment arm 160 is selectively positionable relative to body 110 through rotation of first and second retaining portions 202, 204 in opposite directions. In this manner, a length of spinal fixation device 100 may be tailored to, e.g., the intervertebral space. Elongate adjustment arm 160 includes first and second portions 166, 168 that are selectively adjustable relative to each other. First portion 166 of elongate adjustment arm 160 includes outer threads 162 along a length of first portion 166. Outer threads 162 are configured to engage internal threads 209, 213 of first and second retaining portions 202, 204. First portion 166 includes a plurality of longitudinally aligned bores 167 configured and dimensioned to receive screw 190 therein to secure first portion 166 to body 110. First portion 166 further includes a rod 180 configured to be received in a slot 142 defined in first engaging portion 140. Slot 142 is configured to enable rotation of first engaging portion 140 about rod 180 and slidable engagement of rod 180 within slot 142. Depending on the relative orientation and position of first and second portions 166, 168 of elongate adjustment arm 160, slot 142 slidably engages rod 180, while enabling rotation of first engaging portion 140 about rod 180. Rod 180 has a circular cross-section to enable rotation of first engaging portion 140 about rod 180. Under such a configuration, relative movement of first and second portions 166, 168 changes an angle of first engaging portion 140 with respect to longitudinal axis "A-A" (FIG. 8).

Second portion 168 of elongate adjustment arm 160 includes outer threads 164 configured to engage internal threads 209, 213 of first and second retaining portions 202, 204. Furthermore, second portion 168 includes a plurality of longitudinally aligned bores 169 (FIG. 9) configured to receive screw 190 therein to secure second portion 168 relative to body 110. Second portion 168 includes a rod 182 configured to be received in groove 144 defined in first engaging portion 140. Rod 182 includes a round portion 182a, and groove 144 has a complementary configuration to receive round portion 182a therein. In an embodiment, groove 144 and rod 182 may be configured to enable rotation of first engaging portion 144 about rod 182.

First and second portions 166, 168 of elongate adjustment arm 160 are movable relative to each other, e.g., prior to being threadably assembled with first and second retaining portions 202, 204. In this manner, first engaging portion 140 may be advantageously angled to provide a desired amount of lordosis tailored to the need of each patient. For example, first engaging portion 140 may be positioned substantially orthogonal to the longitudinal axis (FIG. 3) and adjacent second end 126 of body 110. Alternatively, first engaging portion 140 may define an acute angle with longitudinal axis "A-A" (FIG. 8) and spaced apart from second end 126.

Figure 10:
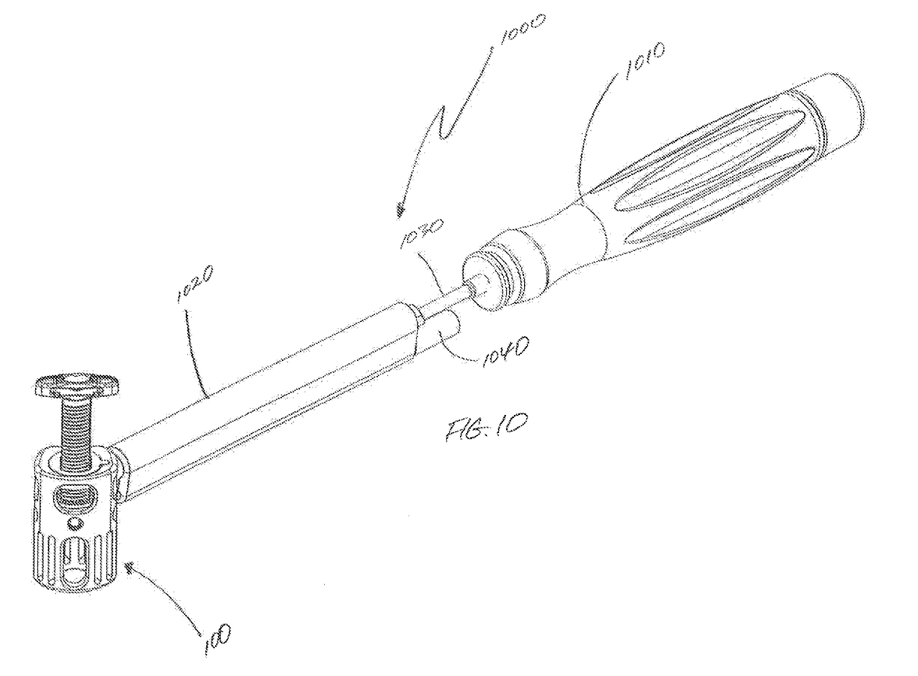
FIG. 10 is a perspective view of a surgical instrument for use with the spinal fixation device of FIG. 1.
Figure 11:
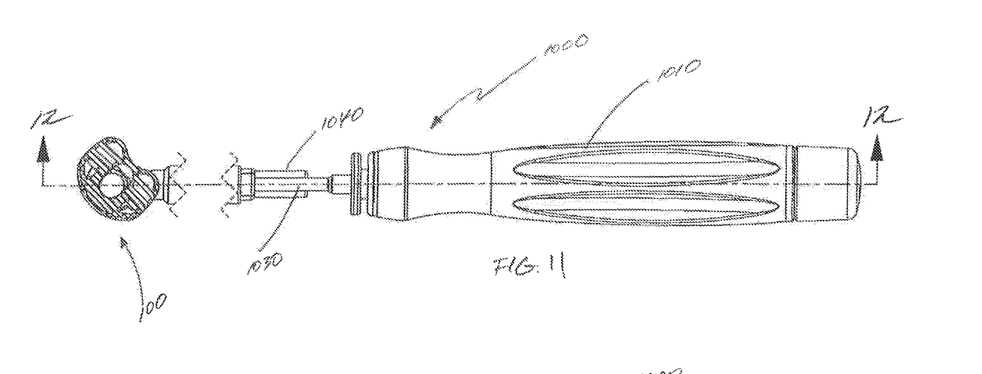
FIG. 11 is a top view of the surgical instrument of FIG. 10.
Figure 12:
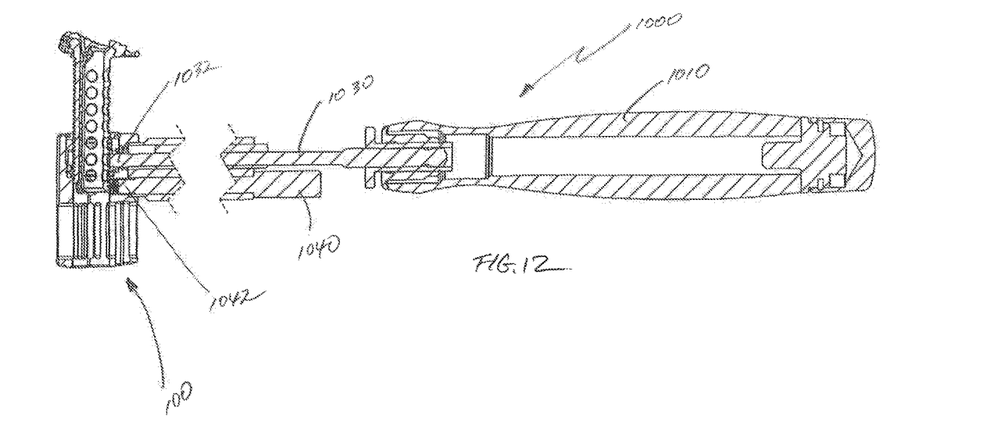
FIG. 12 is a cross-sectional view of the surgical instrument of FIG. 11 cut along a section line "12-12" in FIG. 11.

With reference now to FIGS. 10-12, an embodiment of the present disclosure is shown generally as a surgical instrument 1000 for use with spinal fixation device 100 to position spinal fixation device 100 between adjacent vertebral bodies. Surgical instrument 1000 includes a handle 1010 and an elongate body 1020 extending from handle 1010. Elongate body 1020 includes first and second rods 1030, 1040 rotatably supported with elongate body 1020. First and second rods 1030, 1040 include engaging portions 1032, 1042, respectively. Engaging portion 1042 may be threadably coupled to bore 121 in body 110. Engaging portion 1032 is operatively coupled with teeth 266, 268 of first and second retaining portions 202, 204, such that rotation of handle 1010 causes concomitant rotation of engaging portion 1032 of elongate member 1030. Rotation of engaging portion 1032 causes first and second retaining portions 202, 204 to rotate in opposite directions. Rotation of internal threads 209, 213 of first and second retaining portions 202, 204 causes axial movement of elongate adjustment arm 160. Rotation of handle 1010 in an opposite direction causes axial movement of elongate adjustment arm 160 in an opposite direction. Engaging portion 1032 may be selectively coupled with various drivers including a large driver configured to operatively engage first and second retaining portions 202, 204 to cause axial movement of elongate adjustment arm 160. Alternatively, engaging portion 1032 may be selectively coupled with a small driver configured to engage only one of first and second retaining portions 202, 204 through an eccentric bushing, and thereby enabling adjustment of orientation of first engaging portion 140 with respect to body 110. The eccentric bushing may be keyed in two positions to adjust lordosis or kyphosis. Elongate member 1030 may also define a working channel configured to receive the drivers therethrough. In addition, screws 190 may be received through the working channel. Screw 190 may be secured within bores 167, 169 to fix elongate adjustment arm 160 with body 110.

In use, the clinician first distracts vertebral bodies of interest to establish the intervertebral space. The clinician may then remove vertebral tissue, if necessary or desired. For example, the vertebral tissue may include all or a portion of one or more vertebral bodies. First and second portions 166, 168 of elongate adjustment arm 160 are selectively positioned to achieve a desired orientation of first engaging portion 140. Surgical instrument 1000 is coupled with spinal fixation device 100 by threadably coupling engaging portion 1042 with bore 121. Spinal fixation device 100 is then positioned adjacent a desired intervertebral space between vertebral bodies. Handle 1010 is then rotated to provide concomitant rotation of engaging portion 1032. Handle 1010 is rotated until a desired amount of a length of spinal fixation device 100 is effected through axial movement of elongate adjustment arm 160. Spinal fixation device 100 is then positioned within the intervertebral space between the vertebral bodies of interest. The clinician may make further adjustments to the length of spinal fixation device 100 by rotating handle 1010. In addition, the clinician may use the small driver that is configured to engage only one of first and second retaining portions 202, 204 through an eccentric bushing in order to adjust orientation of first engaging portion 140 with respect to body 110. Thereafter, engaging portions 1032, 1042 are disengaged from bores 121. Screws 190 are inserted into bores 121 and into the respective bores 167, 169 in elongate adjustment arm 160 to lock the orientation of first engaging portion 140 and the length of spinal fixation device 100.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A spinal fixation device comprising:
   a body having first and second ends, the body defining a longitudinal axis, the first end defining an aperture aligned with the longitudinal axis;
   an engaging portion configured to engage a vertebral body; and
   an adjustment member configured to be received in the body through the aperture, the adjustment member including first and second supporting members operatively coupled with the engaging portion, the first supporting member having a camming rod slidably engaging a camming slot defined in the engaging portion, wherein the first and second supporting members are movable relative to each other to selectively position the engaging portion along the longitudinal axis at one orientation out of a plurality of orientations relative to the body.

2. The spinal fixation device according to claim 1, wherein the second supporting member includes a rod, the engaging portion coupled rotatably with the rod.

3. The spinal fixation device according to claim 1, wherein the first supporting member of the adjustment member includes threads disposed along a length of the first supporting member, the threads configured to selectively position the first supporting member at one position out of a plurality of positions along the longitudinal axis defined by the body.

4. The spinal fixation device according to claim 3, wherein the second supporting member of the adjustment member includes threads disposed along a length of the second supporting member, the threads configured to selectively position the second supporting member at one position out of a plurality of positions along the longitudinal axis.

5. The spinal fixation device according to claim 4, wherein the body includes a first retaining member rotatably supported in the body, the first retaining member including internal threads configured to engage the threads on the first and second supporting members.

6. The spinal fixation device according to claim 5, wherein the first retaining member includes a circumferential groove and a radially expandable retaining ring, the radially expandable retaining ring positioned in the circumferential groove.

7. The spinal fixation device according to claim 6, wherein the body includes an annular groove configured to receive at least a portion of the radially expandable retaining ring.

8. The spinal fixation device according to claim 5, wherein the body further includes a second retaining member rotatably supported in the body, the second retaining member including internal threads configured to engage the threads on the first and second supporting members.

9. The spinal fixation device according to claim 8, wherein the first and second retaining members each include a plurality of teeth opposing each other.

10. The spinal fixation device according to claim 9, wherein the first retaining member includes a plurality of teeth extending along the longitudinal axis defined by the body, the plurality of teeth operatively coupled with the first rod of the insertion instrument such that rotation of the first rod causes rotation of the first retaining member about the longitudinal axis, which causes an axial movement of the adjustment member.

11. The spinal fixation device according to claim 1, wherein the body includes a plurality of bores configured to receive a screw.

12. The spinal fixation device according to claim 11, wherein the plurality of bores is arranged circumferentially on side walls of the body.

13. The spinal fixation device according to claim 12, wherein the first supporting member includes a plurality of bores defined along a length thereof.

14. The spinal fixation device according to claim 12, wherein the second supporting member includes a plurality of bores defined along a length thereof.

15. The spinal fixation device according to claim 12, wherein at least one bore out of the plurality of bores defined in the body is aligned with at least one bore out of the bores defined in the first and second supporting members.

16. The spinal fixation device according to claim 1, wherein the second end of the body is configured to engage an adjacent vertebral body.

17. The spinal fixation device according to claim 1, wherein the engaging portion includes a plurality of protrusions configured to grip the vertebral body.

18. The spinal fixation device according to claim 1, wherein movement of one of the first and second supporting members with respect to the other of the first and second supporting members changes an angle of the engaging portion with respect to the longitudinal axis of the body.

19. The spinal fixation device according to claim 1, wherein the adjustment member is movable along the longitudinal axis of the body.

20. The spinal fixation device according to claim 1, wherein the engaging portion defines an acute angle with respect to the longitudinal axis of the body when the engaging portion is positioned in the one orientation.

21. A spinal fixation system comprising:
a spinal fixation device including:
a body defining a longitudinal axis, the body having a first end defining an aperture aligned with the longitudinal axis;
a first engaging portion configured to engage a vertebral body; and
an adjustment member configured to be received in the body through the aperture, the adjustment member including first and second supporting members, the first engaging portion rotatably coupled with the first and second supporting members, the first supporting member having a camming rod slidably engaging a camming slot defined in the first engaging portion, the first and second supporting members movable relative to each other to selectively position the first engaging portion at one orientation out of a plurality of orientations relative to the body, the first engaging portion movable along the longitudinal axis of the body; and
an insertion instrument having an elongate member including first and second rods configured to releasably engage the body.

22. The spinal fixation system according to claim 21, wherein the body includes a pair of bores configured to receive a screw.

23. The spinal fixation system according to claim 22, wherein the first and second rods are configured to engage the pair of bores.

24. The spinal fixation system according to claim 22, wherein the second rod threadably engages one of the pair of bores.

* * * * *